United States Patent
Miyamoto et al.

(10) Patent No.: US 6,276,222 B1
(45) Date of Patent: Aug. 21, 2001

(54) METHOD FOR EVALUATING DETERIORATION OF INSULATING PAPER

(75) Inventors: Teruo Miyamoto; Yoshihiro Makino; Isao Itakura; Hitoshi Anetai, all of Tokyo (JP)

(73) Assignee: Mitsubishi Denki Kabushiki Kaisha, Tokyo (JP)

(*) Notice: Subject to any disclaimer, the term of this patent is extended or adjusted under 35 U.S.C. 154(b) by 0 days.

(21) Appl. No.: 09/230,507
(22) PCT Filed: Jun. 3, 1997
(86) PCT No.: PCT/JP97/01884
§ 371 Date: Jan. 26, 1999
§ 102(e) Date: Jan. 26, 1999
(87) PCT Pub. No.: WO98/56017
PCT Pub. Date: Dec. 10, 1998

(51) Int. Cl.$^7$ ............................ G01N 33/34; G01M 19/00
(52) U.S. Cl. .................................. 73/866; 73/865.9; 436/2
(58) Field of Search ................................. 73/866, 865.9; 436/2

(56) References Cited

U.S. PATENT DOCUMENTS 5,309,766   5/1994   Nanba et al. .
5,309,776 * 5/1994   Nanba et al. .......................... 73/866

FOREIGN PATENT DOCUMENTS 61-150305   7/1986   (JP) .
3-211806    9/1991   (JP) .
4-241407    8/1992   (JP) .
5-055050    3/1993   (JP) .
7-043414    2/1995   (JP) .
8-124751    5/1996   (JP) .

OTHER PUBLICATIONS

"Physicochemical Characterization of the Thermal Aging of Insulating Paper in Power Transformers" by Lessard et al., 1996 IEEE Intl. Symposium on Electrical Insulation, Jun. 1996 pp. 533–537 vol. 2.

"Crystallinity of Electrical Insulating Paper" by Tsuchie et al, Transactions of IEEJ, 101(40, p. 250, 1981 with English summary.

* cited by examiner

Primary Examiner—Jill Warden
Assistant Examiner—Monique T. Cole
(74) Attorney, Agent, or Firm—Sughrue, Mion, Zinn, Macpeak & Seas, PLLC

(57) ABSTRACT

According to the present invention, insulating paper immersed in an oil is heated and deteriorated at a temperature up to 110° C. which is in an operating temperature region for an oil-filled electric apparatus, and the value of the degree of the polymerization which decreases with the deterioration of the insulating paper and amount of carbon dioxide and carbon monoxide which is generated by the heat decomposition of the insulating paper and which is dissolved in the insulating oil are used to observe the generation rate thereof. The present invention is a method of evaluating deterioration characteristics of insulating paper from the change of the degree of polymerization with passage of time and from the temperature dependence of the gas generation rate. The deterioration of the insulating paper has different aspects in the regions higher and lower than 110° C., and the deterioration characteristics of the insulating paper on the low temperature side can be accurately evaluated.

The deterioration of the insulating paper has different aspects in the regions higher and lower than 110° C., and the deterioration characteristics of the insulating paper on the low temperature side can be accurately evaluated.

3 Claims, 2 Drawing Sheets

METHOD FOR EVALUATING DETERIORATION OF INSULATING PAPER

TECHNICAL FIELD

The present invention relates to a method of evaluating the deterioration of insulating paper. In particular, it relates to a method of evaluating deterioration of insulating paper at an operating temperature of an oil-filled electric apparatus such as an oil-filled transformer, an oil-filled reactor or the like, in order to diagnose the life thereof.

BACKGROUND ART

When insulating paper in an insulating oil deteriorates, the decrease in the mechanical strength thereof is quite large, while the decrease in the dielectric breakdown voltage is small. When external short-circuiting occurs in an oil-filled electric apparatus such as an oil-filled transformer, oil-filled reactor or the like, a large electromagnetic mechanical force is generated inside the electric apparatus. Accordingly, from the stand point of the lowered mechanical strength, the life of the electric apparatus has been estimated from the degree of deterioration of the insulating paper used to insulate conductive material.

The degree of deterioration of the insulating paper is evaluated by measuring its tensile strength the degree of polymerization and the like, or by observing the deterioration speed. Evaluating the degree of deterioration of the insulating paper by determining the amount of a component such as furfural, acetoaldehyde, acetone, carbon dioxide, carbon monoxide and the like which is generated by deterioration of the insulating paper is another method currently being studied.

These methods of evaluating the deterioration of insulating paper are carried out by an accelerated deterioration test at an elevated temperature of over a hundred ten degrees centigrade to two hundred degrees centigrade. Generally, an oil-filled electric apparatus is operated at a temperature of not more than 110° C., and the degree of deterioration of the insulating paper is predicted by extrapolating the accelerated deterioration test data obtained at the elevated temperature at the operating temperature of the oil-filled electric apparatus (typically up to 110° C.).

The above-mentioned method in which the high temperature accelerated deterioration test data is extrapolated to 110° C. or less to estimate the degree of the deterioration of the insulating paper presents the following problem.

Water ($H_2O$) and methane ($CH_4$) have the same molecular weight, 18, but the boiling points thereof are very different; that of water is 100° C. and that of methane is −164° C. The difference in the boiling points is felt to result from the hydrogen bond formed in the water molecule. The material of the insulating paper is typically cellulose, which has many hydroxyl groups (—OH) and also since oxygen is an atom having a large electronegativity, that is the capacity for attracting electrons of neighbouring atoms to which the oxygen is bonded, the electron of the hydrogen atom is attracted, the oxygen itself is negatively polarized and the hydrogen is positively polarized. Hydrogen and oxygen also approach each other and hydroxyl groups attract each other to form a physical hydrogen bond. As is shown by the difference in the boiling point of water and methane, the hydrogen bond has a large effect on thermal characteristics. One can expect that a similar phenomenon also occurs in the insulating paper the raw material thereof being cellulose having many hydroxyl groups. That is, one can expect that the mechanism of deterioration of the insulating paper also changes at around 100° C. due to the intervening hydrogen bond.

Accordingly, it became clear that the above-mentioned conventional evaluation method, in which the accelerated deterioration test data obtained at an elevated temperature is extrapolated to the operating temperature of the electric apparatus which is not more than 110° C., has a problem in precision.

Even with the high temperature-accelerated deterioration test which has been conventionally carried out at a temperature of from over a hundred ten degrees centigrade to around two hundred degrees centigrade, several months are required to obtain data; if a deterioration test is carried out at a temperature as low as 60° C., at about which the oil-filled electric apparatus is operated, a period of 10 years or more is required. A test requiring such a long period of time is not always preferable from a practical stand point. However, if the data of the low temperature deterioration phenomenon is different than the data extrapolated from the high temperature deterioration test data, the diagnosis of the life of the oil-filled electric apparatus cannot be accurately carried out based on the results thereof. Accordingly, in order to improve the precision of diagnosing the life of the electric apparatus, a long-term low temperature deterioration test still needs to be carried out.

SUMMARY OF INVENTION

An object of the present invention is to develop a method of evaluating deterioration of insulating paper with high accuracy. The present inventors have found that the specific nature of the insulating paper is such that the insulating paper is less susceptible to deterioration at a low temperature of not more than about 110° C., while it deteriorates more quickly at a temperature higher than this, and achieved the present invention.

That is, the present invention relates to a method of evaluating the degree of deterioration of kraft pulp insulating paper which deteriorates in an insulating oil at a temperature of not more than 110° C., based on the physical and/or chemical properties of said insulating paper.

In a preferred embodiment of the present invention, said physical and/or chemical properties are the polymerization degree or the decomposition rate of the insulating paper.

In another preferred embodiment of the present invention, said polymerization degree is expressed by the following evaluation equation wherein $1925 \leq A \leq 1930$, $3.6 \leq B \leq 3.7$;

$$D = D_0 \times 10^{-N \times 10^{\{-A/(273+t)+B\}}}$$

wherein, D is the polymerization degree of the insulating paper, $D_0$ is the initial polymerization degree of the insulating paper, N is the number of years of heating and t is the heating temperature (° C.).

In still another preferred embodiment of the present invention, said decomposition rate is expressed by the following evaluation equation wherein $15.8 \leq \alpha \leq 14.6$, $10500 \leq \beta \leq 10700$;

$$X = \alpha \exp(-\beta/RT)$$

wherein K is the generation rate (ml/gh) of ($CO_2+CO$), R is 1.987 cal/mol·deg, and T is the absolute temperature (K).

In still another preferred embodiment of the present invention, the time required for said polymerization degree to reach 450 is expressed by the following equation wherein $0.7 \leq X \leq 1.7$, $8200 \leq Y \leq 8800$;

$$\theta = X \exp(-Y/RT)$$

wherein θ is the time (h) required for the polymerization degree to reach 450, R is 1.987 cal/mol deg and T is the absolute temperature (K).

DETAILED DESCRIPTION OF INVENTION

The raw material of the insulating paper used according to the present invention comprises cellulose. Cellulose is a polysaccharide represented by $(C_6H_{10}O_5)_n$, in which glucose units are linked by β-1,4 glycoside bond. The degree of polymerization refers to the number n, and can be determined by measurement of the viscosity of a copper/ethylene diamine solution thereof.

Insulating paper decomposes when heated in an insulating oil at a predetermined temperature and the degree of polymerization thereof is lowered. The deterioration of the insulating paper can be evaluated based on the equation derived from the graph obtained by plotting the relationship between the heating time and the change in polymerization degree at a predetermined temperature.

Since carbon dioxide gas ($CO_2$) and carbon monoxide gas (CO) are generated by the decomposition of the cellulose, the amount of $CO_2$ and CO generated per unit of time is measured at a predetermined heating temperature to calculate the ($CO_2$+CO) generation rate. Then the change of the gas generation rate is plotted at each heating temperature, and the deterioration of the insulating paper can be evaluated based on the equation derived from the graph obtained.

The present invention will be explained in detail based on the following examples.

EXAMPLE 1

Figure 1:
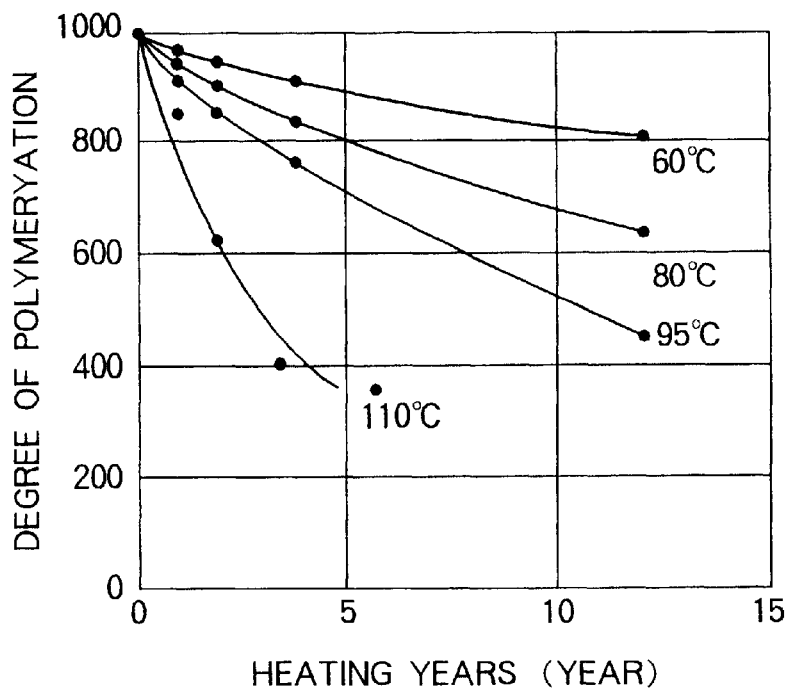
FIG. 1 is a graph showing the relationship between the degree of polymerization of the insulating paper and the heating years according to Example 1 of the present invention.

The insulating paper used for insulation in an oil-filled electric apparatus is typically made of kraft pulp. Accordingly, in a low temperature deterioration test, fully dried kraft pulp insulating paper (polymerization degree: 1000) was put in a degassed insulating oil and sealed, then heated in an oven at 60° C., 80° C., 95° C. and 110° C. In each oven, a plurality of sealed tanks were prepared and the sealed tanks were taken out after they had been heated for an appropriate length of time (years), and the insulating paper was subjected to a measurement of the degree of polymerization, and the carbon dioxide gas and carbon monoxide gas in the oil were analyzed (an outline of the analysis of the gas in the oil will be given later in the illustration of FIG. 2). The tests at a temperature of 60° C., 80° C., and 95° C. were carried out, at longest, for 12 years and the relationship between the polymerization degree and the heating years was examined. The results are given in FIG. 1. FIG. 1 shows that the polymerization degree is lowered with the passage of the heating time and that the higher the heating temperature is, the faster the lowering speed of the polymerization degree is lowered. The results of FIG. 1 can be expressed by the following equation (1).

$$D = D_0 \times 10^{-N \times 10^{\{-A/(273+t)+B\}}} \quad (1)$$

$$1925 \leq A \leq 1930, \ 3.6 \leq B \leq 3.7$$

wherein, D is the polymerization degree of the insulating paper, $D_0$ is the initial polymerization degree of the insulating paper, N is the number of years of heating (year) and t is the heating temperature (° C.).

When the insulating paper is thermally decomposed, carbon dioxide gas ($CO_2$) and carbon monoxide gas (CO) are generated and these gasses are dissolved in the insulating oil. The gas dissolved in the oil can be extracted and subjected to gas analysis with a gas chromatograph.

The generation rate of these gasses is represented by the sum of the amount of $CO_2$ and CO generated per gram of insulating paper per hour. In other words, since the generation rate is related to the decomposition rate of the insulating paper, the degree of deterioration of the insulating paper and the amount of the gas dissolved in the oil are correlated. The degree of deterioration of the insulating paper can be estimated from this correlation.

Figure 2:
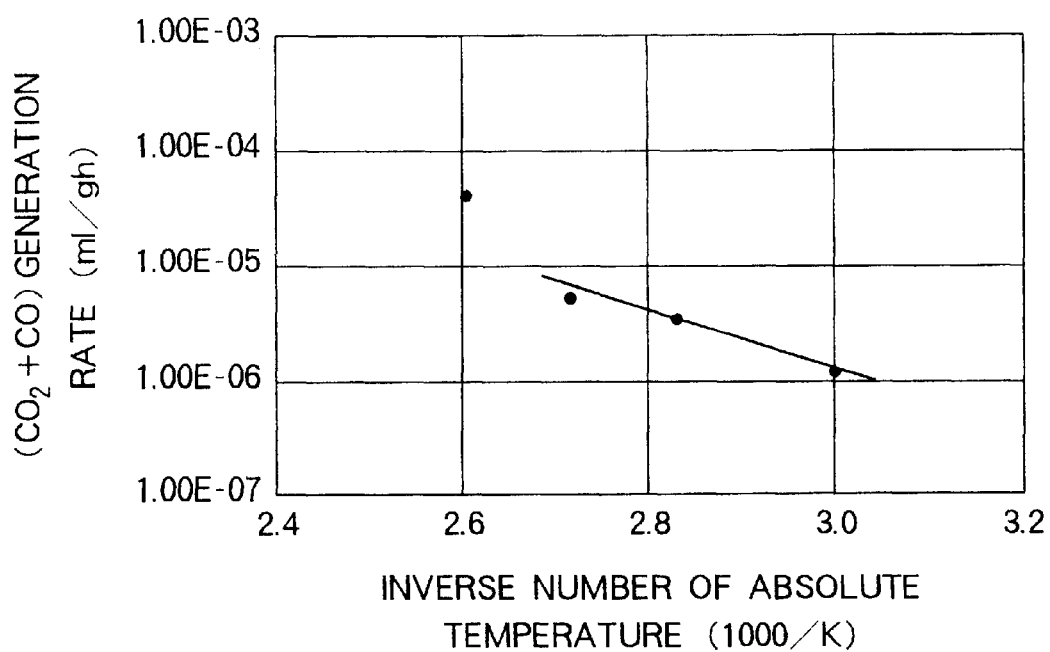
FIG. 2 is a graph showing the temperature dependence of ($CO_2$+CO) generation rate according to Example 1 of the present invention.

FIG. 2 illustrates the temperature dependence of the ($CO_2$+CO) generation rate. The result is expressed by the following equation (2).

$$K = \alpha \exp(-\beta/RT) \quad (2)$$

$$15.8 \leq \alpha \leq 14.6, \ 10500 \leq \beta \leq 10700$$

wherein K is the ($CO_2$+CO) generation rate (ml/gh), R is 1.987 cal/mol deg, and T is the absolute temperature (K).

EXAMPLE 2

In order to confirm whether the low temperature deterioration test data and the high temperature deterioration test data can be shown in the same graph, the high temperature deterioration test was also carried out.

As a method of evaluating deterioration of insulating paper, the high temperature deterioration test was carried out by preparing samples as sealed tanks in the same manner as that used for the low temperature deterioration test and the tanks were heated in an oven at 130° C., 150° C. and 180° C. respectively to determine the relationship between the polymerization degree of the insulating paper and the heating years. As for the time required for the polymerization degree to reach 500, the high temperature deterioration test data and the low temperature deterioration test data were combined into one graph and the temperature dependence is shown in FIG. 3.

Figure 3:
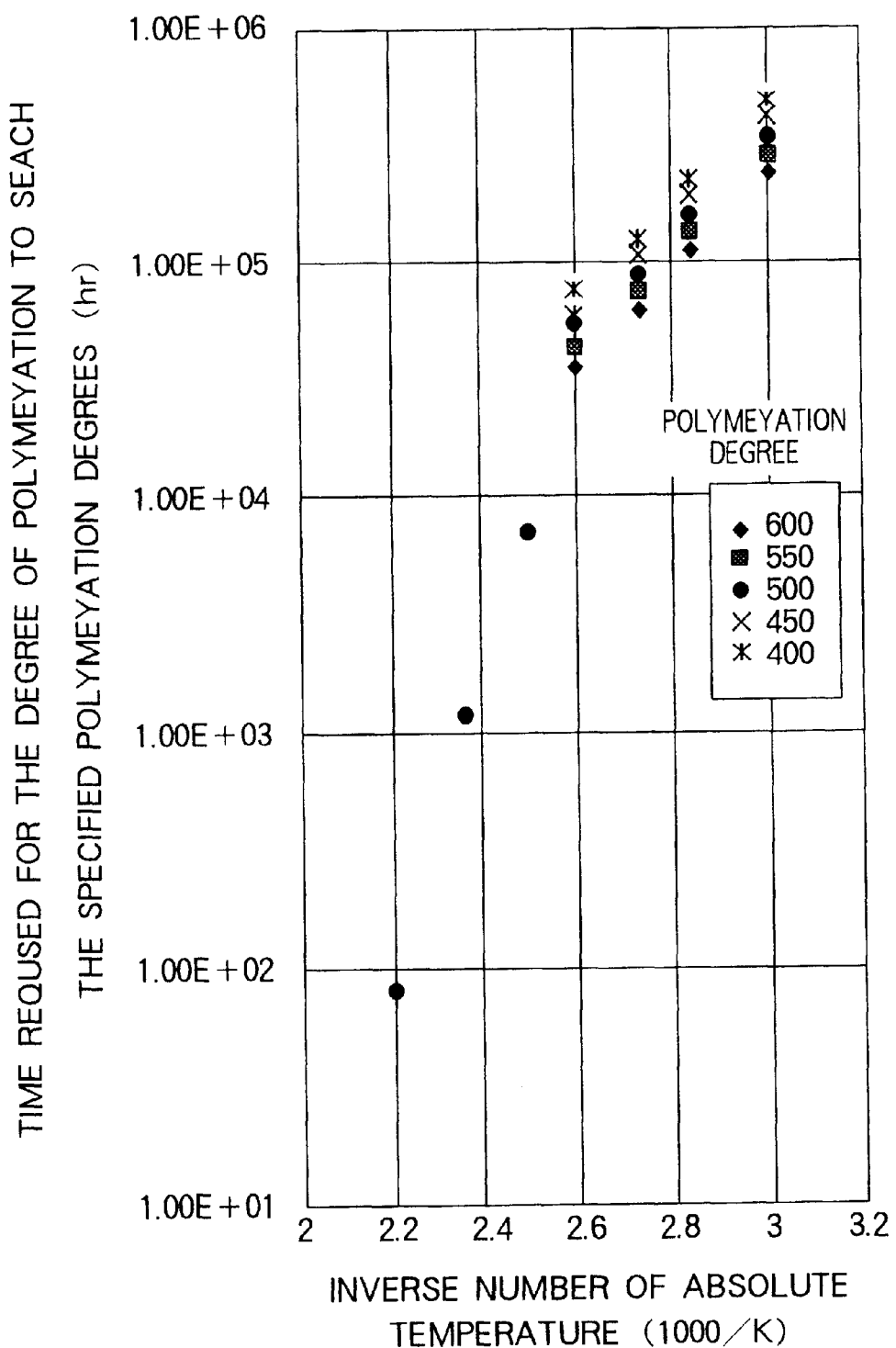
FIG. 3 is a graph showing the temperature dependence of the time required for the polymerization degree of the insulating paper to reach 600, 550, 500, 450, and 400, according to Example 1 of the present invention.

As for the low temperature deterioration test, in addition to the time required for the polymerization to reach 500, the temperature dependence of the time required for the polymerization degree to reach 400, 450, 550 and 600 are also shown in FIG. 3. Among these, the time required for the polymerization degree to reach 450 can be expressed by the following equation (3).

$$\theta = X \exp(-Y/RT) \quad (3)$$

$$0.7 \leq X \leq 1.7, \ 8200 \leq Y \leq 8800$$

wherein θ is the time (h) required for the polymerization degree to reach 450, R is 1.987 cal/mol·deg and T is the absolute temperature (K).

As FIG. 3 illustrates, no straight line on the low temperature side of the Arrhenius plot is found in the region obtained by extrapolation from the high temperature side and the line bends at about 110° C. The slope of the line is gentler on the low temperature side than the high temperature side. This shows that the insulating paper deteriorates easier at a high temperature and less easily at a low temperature.

Accordingly, as mentioned above, it is understood that the effect of the hydrogen bond is also imparted to the deterioration of the insulating paper. That means, the results of FIG. 3 show that it is impossible to estimate the degree of deterioration of the insulating paper by extrapolating the high temperature deterioration test data at the operating temperature of an oil-filled electric apparatus.

Therefore, we can now estimate the degree of deterioration of the insulating paper at the operating temperature of an oil-filled electric apparatus with high precision from FIG. 1, FIG. 2 and FIG. 3, obtained from the low temperature deterioration test.

It goes without saying that the equations (1)–(3) can be represented as other evaluation equations; the equation (1) can be expressed as an exponential function, or equation (2) and equation (3) can be represented using common logarithms.

Recently, a method of evaluating the degree of deterioration of insulating paper by means of furfural, generated when the insulating paper decomposes, is also under examination. Nevertheless, the degree of deterioration is connected to the polymerization degree, i.e., the concept of the low temperature deterioration evaluation method is inevitable in this method as well.

Conventionally, high temperature accelerated deterioration test data obtained at from over a hundred ten degrees centigrade to two hundred degrees centigrade, has been extrapolated at the operating temperature of an oil-filled electric apparatus to estimate the degree of deterioration of the insulating paper. Nevertheless, with the high temperature deterioration test and the low temperature deterioration test of 12 years, the present invention made it clear for the first time that the insulating paper shows different heat deterioration phenomena on the temperature side higher than around 110° C. than on the temperature side lower than around 110° C. Consequently, the conventional estimation method gives poor estimation accuracy of the degree of deterioration of the insulating paper.

Therefore, the low temperature deterioration test data of the present invention which is-in the operating temperature region of an oil-filled electric apparatus allows evaluation of deterioration of the insulating paper with high precision, hence the industrial significance of the present invention is great.

What is claimed is:

1. A method of evaluating deterioration of insulating paper, the method comprising subjecting kraft insulating paper to insulating oil at a heating temperature of not more than 110° C. to deteriorate said kraft pulp insulating paper and to determine physical and/or chemical properties of said kraft pulp insulating paper in order to use said physical and/or chemical properties as an index, wherein said physical and/or chemical properties are the polymerization degree or the decomposition rate of the insulating paper;

the method further comprising measuring the heating temperature and the time (years) of heating, and calculating the polymerization degree, said polymerization degree being expressed by the following evaluation equation:

$$D = D_0 \times 10^{-N \times 10^{\{-A/(273+T)+B\}}}$$

wherein, $1925 \leq A \leq 1930$, $3.6 \leq 5 \leq 3.7$; D is the polymerization degree of the insulating paper, $D_0$ is the initial polymerization degree of the insulating paper, N is the number of years of heating and t is the heating temperature (° C.).

2. A method of evaluating deterioration of insulating paper, the method comprising subjecting kraft insulating paper to insulating oil at a heating temperature of not more than 110° C. to deteriorate said kraft pulp insulating paper and to determine physical and/or chemical properties of said kraft pulp insulating paper in order to use said physical and/or chemical properties as an index, wherein said physical and/or chemical properties are the polymerization degree or the decomposition rate of the insulating paper;

the method further comprising measuring the absolute temperature (K), and calculating the decomposition rate, said decomposition rate being expressed by the following evaluation equation:

$$X = \alpha \exp(-\beta/RT)$$

wherein, $14.6 \leq \alpha \leq 15.8$, $10500 \leq \beta \leq 10700$; X is ($CO_2+CO$) generation rate (ml/gh), R is 1.987 cal/mol·deg, and T is the absolute temperature (K).

3. A method according to claim 1, or claim 2, the method further comprising measuring the absolute temperature (K), and calculating the time required for said polymerization degree to reach 450, the time required for said polymerization degree to reach 450 being expressed by the following evaluation equation:

$$\Theta = X \exp(-Y/RT)$$

wherein, $0.7 \leq X \leq 1.7$, $8200 \leq Y \leq 8800$; $\Theta$ is the time (h) required for the polymerization degree to reach 450, R is 1.987 cal/mol deg and T is the absolute temperature (K).

* * * * *